(12) United States Patent
Larson et al.

(10) Patent No.: US 6,302,848 B1
(45) Date of Patent: Oct. 16, 2001

(54) IN VIVO BIOCOMPATIBLE ACOUSTIC COUPLING MEDIA

(75) Inventors: Margaret J. Larson, Lummi Island; John W. Rutter, Bellingham; Larry L. Smith, Seattle, all of WA (US)

(73) Assignee: Sonotech, Inc., Bellingham, WA (US)

( * ) Notice: Subject to any disclaimer, the term of this patent is extended or adjusted under 35 U.S.C. 154(b) by 0 days.

(21) Appl. No.: 09/346,463

(22) Filed: Jul. 1, 1999

(51) Int. Cl.$^7$ .................................................. A61B 8/00
(52) U.S. Cl. ............................................ 600/461; 600/438
(58) Field of Search .................................. 600/437, 458, 600/460, 438, 461; 424/450

(56) References Cited

U.S. PATENT DOCUMENTS

| | | |
|---|---|---|
| 4,002,221 | 1/1977 | Buchalter . |
| 4,459,854 | 7/1984 | Richardson et al. . |
| 4,593,699 | 6/1986 | Poncy et al. . |
| 4,994,227 | 2/1991 | Dietz et al. . |
| 5,078,149 | 1/1992 | Katsumata et al. . |
| 5,093,319 | 3/1992 | Higham et al. . |
| 5,259,383 | 11/1993 | Holstein et al. . |
| 5,266,326 | 11/1993 | Barry et al. . |
| 5,342,617 | 8/1994 | Gold . |
| 5,405,366 | 4/1995 | Fox et al. . |
| 5,676,159 | 10/1997 | Navis . |
| 5,873,367 * | 2/1999 | Buchalter .............................. 128/898 |
| 6,146,657 * | 11/2000 | Unger et al. ......................... 424/450 |

FOREIGN PATENT DOCUMENTS 55-63636    5/1980  (JP) .

OTHER PUBLICATIONS

Doelker, E., "Water Swollen Cellulose Derivatives in Pharmacy", *Hydrogels in Medicine and Pharmacy: vol. 2—Polymers*, edited by Peppas, N. A., CRC Press Inc., Boca Raton, Florida, 1987, p. 124.
WPI—Japanese Patent Abstract JP55063636.
WPI—Japanese Patent Abstract JP3114453.

* cited by examiner

*Primary Examiner*—Marvin M. Lateef
*Assistant Examiner*—Maulin Patel
(74) *Attorney, Agent, or Firm*—Robert L. McDowell

(57) ABSTRACT

A medical ultrasound coupling media and lubricant, in gel or liquid form, comprised of polyethylene oxide (PEO), and aqueous solvent solutions. The inventive coupling media provides long term biocompatibility (bio-inert, bio-erodable or biodegraded and excreted) in vivo with human tissue and body fluids. The ultrasound coupling and lubricating media is formulated and manufactured in such manner and form that renders the acoustic media sterile, non-cross-linked, pseudoplastic, and containing acceptably low levels of pyrogens.

9 Claims, No Drawings

IN VIVO BIOCOMPATIBLE ACOUSTIC COUPLING MEDIA

FIELD OF THE INVENTION

The present invention is directed toward the medical use of acoustic coupling gels and fluids used in ultrasound imaging and doppler based flow measurement procedures that invade the body, such as ultrasound guided biopsy, ophthalmic imaging, during surgery and intracavity examinations.

BACKGROUND OF THE INVENTION

It is well known to introduce chemical substances into a body in which the chemical substances contact body tissue. One obvious example is introducing medication in pill form into a human or animal. Aside from the particular active ingredient, the pill may comprise different types of waxes, fats, and filler or wetting agents, all of which must not react with body tissue. One such example can be found in U.S. Pat. No. 4,994,227 to Dietz et al.

In medical procedures such as surgery, it is known to introduce chemical substances into a body cavity and in contact with vital tissues. One such example is disclosed in U.S. Pat. No. 5,093,319 to Higham et al. where adhesion or inflammation of tissues after surgery is prevented by placing a material made up of biodegradable derivatives of chitin between the tissues. Another example of the prevention of post-operative adhesions is found in U.S. Pat. No. 5,266,326 to Barry et al. where polysaccharides, such as alginates, and a complexing agent, such as calcium chloride, are combined in situ between affected tissues to form a biodegradable gel. U.S. Pat. No. 5,405,366 to Fox et al. teaches the production of cohesive, non stringy cross-linked gels for the delivery of therapeutic drugs to wound sites by subjecting solutions, such as that of polyethylene oxide in combination with other compounds, to high energy radiation.

With some current surgical procedures, as the uses and technology of medical ultrasound imaging have evolved, imaging procedures that were once performed externally over skin surfaces are now being performed in contact with organs, tissue and body cavity mucosa. For example, when imaging the liver during surgery, the transducer is often placed directly on its surface.

Ultrasound, as used for medical applications, utilizes high frequencies, typically between 1 and 20 MHz for imaging and flow measurements, which are poorly transmitted by air and requires a coupling or conduction medium similar in acoustic properties to tissue, commonly a thick fluid or gel, to transfer the acoustic energy between the body and the electronics. The ultrasound coupling gel or fluid displaces air and fills contours between the piezoelectric transducer or "eye" of the instrument, which converts energy between electrical and acoustic, and the body into which the sound is being directed. This gel or fluid material, by nature of its physical and acoustic properties, serves as an ultrasound acoustic coupler between the body and the electronic transducer, thereby acoustically joining the two, so that the ultrasound based information developed, can freely pass back and forth between the body and the transducer. The gel or fluid material may also serve as a lubricant to aid in the introduction of a medical device used for imaging, such as endoscopes, into the body.

Because of the coupling effect, this media is commonly referred to as an ultrasound couplant, ultrasound gel, ultrasound transmission media or acoustic transmission media. Many fluids and water-based gels have been used as ultrasound couplants over the years. Early use of mineral oil was replaced by gels of water and acrylic based polymers such as CARBOPOL® (a registered trademark of BF Goodrich Specialty Chemicals) typical of those described in U.S. Pat. No. 4,002,221 to Buchalter, and also gels made from acrylic polymers and attached as coupling members to transducers such as are described in U.S. Pat. No. 4,459,854 to Richardson et al. as a method for improvement of perivascular blood flow measurement.

Use of currently available ultrasound coupling fluids and gels of prior art in surgical, and ultrasound guided needle puncture procedures have fundamental disadvantages that place the patient at risk. Some of these disadvantages are described below:

1. Oils or thickened water-based gels typically used in medical ultrasound are similarly described as in previously discussed U.S. Pat. No. 4,002,221, and are comprised of chemical compounds such as acrylic polymers, carboxy alkyl cellulose, hydroxyethylcellulose, carboxy polymethylene, polyalkylene glycol humectants, organic acids, alkali metal salts, parabens and other germicidal and fungicidal agents, and surfactants that are unsuitable for use in applications where they may be carried into the body tissue or fluids.

2. The above-mentioned couplants are also commercially available in sterilized form, thus implying and encouraging their inappropriate use in vivo where their chemical constituents are either known to be harmful to the human body or have not been evaluated for their in vivo use.

3. Currently available ultrasound couplants supplied in sterile form contain acrylic polymers such as CARBOPOL as a common and primary ingredient. CARBOPOL, for example, has not been tested for in vivo biocompatibility. Some currently available sterile couplants also contain cellulose ethers to increase salt stability. According to E. Doecker in "Water Swollen Cellulose Derivatives in Pharmacy" from *Hydrogels in Medicine and Pharmacy: Vol. 2— Polymers,* edited by Peppas N. A., CRC Press Inc., Boca Raton, Fla., 1987, pg. 124, "In common use, such celluloses are used orally and externally, however parenteral administration of celluloses is not recommended since derivatives are not easily metabolized". Since various chemicals of these formulations are not in vivo biocompatible, they can remain in the body as substances that can cause inflammation, disruption in flow of lymph, irritation, anaphylactic shock and other immune system reactions. This concern becomes apparent during ultrasound guided needle biopsy or aspiration, or inside the body when ultrasound transducers encapsulated in fragile sheaths containing sterile ultrasound couplant are inserted for imaging during surgery in direct contact with organs, tissue and blood.

Of additional concern are the unknown chemical constituents formed during sterilization processing. Methods of couplant sterilization include steam autoclave, E-beam, broad spectrum light and gamma radiation protocols. Couplant products that incorporate CARBOPOL in the formulation can break down as a result of heat during autoclaving. When exposed to ionizing radiation, such as in the case of gamma and E-beam, and high intensity light sterilization, free radicals can be formed, and chain scission and cross linking of the polymer can occur, as evidenced by presence of bubbles and changes in color, viscosity and mechanical properties of the polymer products.

It is important to note that sterility of a substance does not guarantee that it is biocompatible, or of greater importance, in vivo biocompatible. When a substance is sterile, it does not contain live microorganisms; however, such sterile materials may not be in vivo-biocompatible should they contain compounds that are incompatible with tissue or body fluids. For example, natural and synthetic materials that are recognized by the FDA as GRAS (Generally Regarded As Safe), may not be in vivo biocompatible. An in vivo biocompatible substance is both sterile, containing no living micro-organisms, and contains no chemicals or substances that are toxic or cause inflammation or immune system reactions, such as from pyrogens, within the living human body. A substance such as the device of this invention is in vivo biocompatible as an ultrasound couplant in contact with human tissue and body fluids.

4. In instances where sterile latex rubber or synthetic "sheaths" containing thickened chemical ultrasound coupling gels are used to encapsulate the ultrasound transducer during surgery, such as described in U.S. Pat. No. 5,259,383 to Holstein et al.; U.S. Pat. No. 4,593,699 to Poncy et al. and U.S. Pat. No. 5,676,159 to Navis; tearing, cutting, or rupture of the sheath can result in the bio-incompatible ultrasound couplant spilling into the body cavity. During procedures such as transcutaneous biopsy or aspiration of fluid under ultrasound imaging guidance, such bio-incompatible ultrasound couplants of the prior art are placed directly on the skin covering the area of the biopsy. A biopsy needle can carry such chemicals into the body, such as into the breast or into amniotic fluid.

It is an object of the present invention to provide an ultrasound couplant and device lubricant suitable for the medical use of ultrasound acoustic energy for imaging and doppler based flow measurement, while contacting body tissue, fluids and organs, during transcutaneous biopsy and fluid aspiration, and to lubricate the passage of the imaging device into body cavities.

It is a further object of the present invention to provide gels and fluids that are in vivo biocompatible, and suitable for use in diagnostic ultrasound procedures inside the body of a human during surgery, guided biopsy, within body cavities and ophthalmic imaging.

SUMMARY OF THE INVENTION

The device of this invention is an in vivo biocompatible lubricant and ultrasound coupling fluid or gel in a non-cross-linked form, produced from compounds based on polyethylene oxide (PEO), and in particular PEO in pure form, that are biodegradable or bio-inert, having known and acceptable biological effects on tissue and the immune system of the human body. The inventive couplant fluid or gel may additionally contain polyalkylene glycol. The inventive couplant fluid or gel can remain in the body or be excreted from the body after being eroded, metabolized or absorbed via natural pathways and processes. In sterile form, the inventive in vivo biocompatible couplant and device lubricant is intended for use in contact with organs, tissue and body fluids during surgery, intracavity, and ultrasound guided needle puncture procedures. The inventive couplant renders acceptable low levels of artifact, distortion and attenuation of ultrasound energy.

In instances where an ultrasound probe is covered by a protective sheath as previously mentioned, the ultrasound couplants of the present invention not only provide acceptable acoustic coupling properties on the outside of the protective sheath but also within the sheath (i.e. between the ultrasound probe and the sheath). Thus, in the event of rupture of the sheath, introduction of the inventive ultrasound couplant into the body in contact with tissue, organs and fluids, will not adversely affect the patient due to the in vivo biocompatibility of the couplants of the present invention.

In the same manner, puncture procedures under ultrasound imaging guidance, such as needle biopsies, can benefit from the present invention in that the ultrasound couplant carried by the needle into the body will be an in vivo biocompatible couplant, thus posing no harm to tissue and organs.

For use in intraoperative procedures, the inventive couplant is placed inside the protective probe cover to couple the ultrasound acoustic energy between the active area of the probe and the cover or sleeve. Since during a surgical or intracavity ultrasound examination, the external surface of the probe cover is in contact with body fluids that naturally conduct acoustic energy, additional couplant on the external surface is seldom required. For intracavity, i.e. vaginal, rectal and transesophageal ultrasound examinations, a lubricant is often required on the transducer and its shaft prior to introduction into the body cavity. When such couplants are used for transcutaneous scanning, ophthalmic imaging or ultrasound guided needle punctures, such as amniocentesis and transcutaneous biopsy procedures, additional couplant is required to couple sound between the external surface of the protective cover or sleeve and the patient. Such couplant is usually placed on the skin of the patient in the area of interest.

As stated above, the compound that achieves the objectives of this invention, that is, possesses in vivo biocompatibility, is polyethylene oxide (PEO). Polyethylene oxide, in amounts varying between 0.05 and 65% by weight, and the balance water, preferably pyrogen free water, and optionally further including polyalkylene glycol in the amounts varying between of 1.0 and 45% by weight, exhibits acoustic properties similar to that of human tissue, renders acceptable low levels of artifact, distortion and attenuation of the ultrasound energy, and acceptable viscosity, film forming and adherence characteristics.

DETAILED DESCRIPTION OF THE INVENTION

The present invention is directed toward the medical use of acoustic coupling fluids and gels used in vivo ultrasound imaging, doppler based flow measurement and in ultrasound guided transcutaneous biopsy.

The present invention is a medical device lubricant and ultrasound coupling media in a non-cross-linked gel or liquid form, comprised of polyethylene oxide (PEO and water, with known and acceptable long term interaction in vivo and is manufactured in such manner and form that renders the acoustic media sterile and biocompatible with human tissue, organs and body fluids.

A group of compounds based on polyethylene oxide (PEO) and in particular PEO in pure form, as a solution in water and containing acceptably low levels of pyrogens, is the preferred composition that demonstrates the desired in vivo biocompatibility and known in vivo biodegradability. Polyethylene oxide based biocompatible compounds and gels when properly formulated with water, or alternatively, PEO in combination with water and a polyalkylene glycol, have acoustic properties similar to that of human tissue, and render acceptable low levels of artifact, distortion and attenuation of the ultrasound energy.

In the preferred embodiment of this invention, PEO is prepared in solution with pure, pyrogen free water. PEO in concentration amounts of about 0.05% to about 65% by weight and of various molecular weights, in the range of about 100,000 to about 8,000,000, can be used to form pseudoplastic solutions tailored to rheological properties desired for the application. As a modification to this base formulation, a polyalkylene glycol containing 2 to 12 carbons, preferably propylene glycol, in a wt. % range of 1 to 45% is incorporated in the formulation. Propylene glycol is biocompatible, and biodegradable and in the preferred embodiment functions as a humectant to increase drying time, and as a preservative and stabilizer that enhances the shelf life of PEO solutions.

In order to produce a biocompatible ultrasound couplant from PEO that has acceptable low levels of artifact, distortion, and attenuation, the couplant must be produced essentially free of air bubbles, undissolved polymer or insoluble particulate material. Application of Good Manufacturing Procedures (GMP) and use of NF PEO, USP propylene glycol, and pyrogen free water are recommended to ensure finished product quality.

Proper blending techniques are necessary to facilitate solution of the polymer in water. Properties that affect ease of solution include molecular weight, polymer concentration, rate of viscosity increase, rate of addition, particle size and the type and speed of agitation employed. It is necessary to obtain good dispersion of the polymer before the viscosity increases to a point where the resin cannot be further dispersed without introduction of high shear. On a laboratory scale, a multi-propeller stirrer is used to create a large vortex at about 600 rpm, followed by addition of POLYOX (PEO resin manufactured by Union Carbide) at a rate that fully disperses the resin. Once dispersion is achieved, the stirring rate is reduced to 50 to 60 RPM and stirred for 30 to 60 minutes until the solution is homogenous. When larger quantities of resin need to be dissolved, particularly if dry resin is added directly to water, equipment such as an eductor/disperser and multi-propeller or standard turbine type stirrers are recommended for ease of solution.

When alkylene glycols are incorporated into the formulation alternative production methods can be used that facilitate efficient addition and dispersion of the polymer. A PEO slurry is first prepared by blending the dry polymer with the polyalkylene glycol, followed by addition of this polymer slurry directly into water while stirring, thus reducing dust and the tendency to clump as is common to direct addition of polymer to water.

Techniques successful in limiting and removing entrapped air from PEO solutions involve a "de-airing" of the water used in the solution. This is accomplished by heating and holding at 60° C. for 2 hours followed by addition of the PEO. In practice, if cooling is desired, accelerated cooling of the water limits the amount of gases that re-absorb. Removal of air entrapped during addition of PEO polymer and high-speed stirring is accomplished by applying a minimum of 25 inches of vacuum subsequent to addition of the polymer and during the period when the polymer is in the process of solvation.

For use as in vivo biocompatible ultrasound couplants, the polymer solution must be sterilized. The common and acceptable sterilization methods of post-production autoclaving and gamma irradiation tend to be unsuitable for polyethylene oxide formulations. Radiation dosages prescribed for sterilization protocols, generally 15 KGY and above, are sufficient to cross-link polyethylene oxide solutions. Such cross-linking decreases lubricity and pseudoplastic behavior creating insoluble solids and cohesive masses that are unsuitable for ultrasound imaging procedures. As an example, U.S. Pat. No. 5,405,366 to Fox et al. teaches methods to produce cross-linked polyethylene in combination with other compounds such as PVA and gylcols, by subjecting combinations of these compounds to high energy radiation sufficient to form cross-linked compounds that are non-stringy and cohesive. Such cross-linked compounds lack the physical properties preferred for use as ultrasound couplants and lubricants.

The embodiment of the present invention describes pseudoplastic, non cross-linked solutions of PEO, water and alternatively, glycols, that are preferably sterilized by heat to avoid cross-linking.

PEO also demonstrates inverse solubility that results in precipitation of PEO from solution at 100° C. This precipitate re-hydrates with time, forming layers of polymer with varying viscosities, however, the uncertainty of product quality after an autoclave and cooling cycle limits the usefulness of conventional autoclave sterilization for products of this invention. Given the constraints on sterilization by the reaction characteristics of PEO, post production sterilization of the final package by high energy sources or autoclave protocols is not practical. As an alternative to conventional post production high energy or autoclave sterilization, PEO formulations can be sterilized in bulk using autoclave protocols, prior to aseptic filling and packaging.

One such method integrates production and sterilization of the polymer solution by use of a reactor vessel suitable for compounding the formula, vacuum degassing and heating the solution, under pressure, to a core temperature of 121° C. In practice, the polymer is compounded in pyrogen free water or alternatively with water and a polyalkylene glycol, heated to 60° C., and degassed under vacuum while stirring. While remaining under seal, the reactor vessel is back-filled with nitrogen gas, the solution heated to 121° C., held for 15 to 30 minutes at temperature and allowed to cool below 100° C. while stirring to achieve a homogenous solution prior to aseptic filling and packaging.

The following examples illustrate preferred compositions and formulations that can be used to prepare solutions of PEO, suitable for use in medical ultrasound procedures. Those skilled in the art recognize that many variations are possible without violating the scope and spirit of the invention together with all changes and modifications to the invention.

PEO used in the embodiments of this invention are selected from Union Carbide Sentry NF POLYOX WSR (water soluble-resins) grades. Formulations were prepared from grades that represent a range of molecular weights that produce solutions of PEO suitable for use as ultrasound couplants of this inventive device. These solutions each have acceptable viscosities (for example in the range of 1,000 to 250,000 centipoise) and mechanical properties, which produce an in vivo biocompatible ultrasound couplant that has acoustic properties similar to that of a target tissue (e.g. human tissue), and which render acceptable low levels of artifact, distortion and attenuation of the ultrasound energy.

Sentry (trade name of Union Carbide) NF grades (National Formulary Standard) of POLYOX selected for embodiments for this device are the WSR N-10 (100,000 mw.), WSR N-80 (200,000 mw.), WSR N-750 (300,000 mw.), WSR-205 (600,000 mw.), WSR 1105 (900,000 mw.), WSR N-60K (2,000,00 mw.), WSR 301 (4,000,000 mw.), and non-NF, WSR-308, (8,000,000 mw.), all of which are soluble in water at room temperature.

Using the manufacturing procedures previously outlined, solutions having various concentrations of WSR N-10, WSR N-80, WSR N-750, WSR 205, WSR 1105, WSR N-60K, WSR 301, and WSR-308 were prepared to determine their properties with changes in polymer concentration as well as to compare the relative differences between the solutions made from each of the grades.

Formulations within the ranges (wt. %) of the following examples were prepared:

EXAMPLE 1

Grade WSR N-10 PEO, Molecular Weight 100,000
Polymer Concentration Range: 10 to 35 wt. %
Formula using WSR N-10
35% WSR N-10
65% pyrogen free water

EXAMPLE 2

Grade WSR N-80 PEO, Molecular Weight 200,000
Polymer Concentration Range: 8 to 20 wt. %
Formula using WSR N-80
15% WSR N-80
85% pyrogen free water

EXAMPLE 3

Grade WSR N-750, PEO, Molecular Weight 300,000
Polymer Concentration Range: 5 to 15 wt. %
Formula using WSR N-750
5% WSR N-750
95% pyrogen free water

EXAMPLE 4

Grade WSR 205, PEO, Molecular Weight 600,000
Polymer Concentration Range: 2 to 10%
Formula using WSR 205
4.5% WSR 205
95.5% pyrogen free water

EXAMPLE 5

Grade WSR 205, PEO, Molecular Weight 600,000
Polymer Concentration Range: 2 to 10%
Propylene Glycol: 1 to 45%
Formula using WSR 205
4% WSR 205
18% USP propylene glycol
78% pyrogen free water

EXAMPLE 6

Grade WSR 1105, PEO, Molecular Weight 900,000
Polymer Concentration Range: 2 to 15 wt. %
Formula using WSR 1105
3.75% WSR 1105
96.25% pyrogen free water

EXAMPLE 7

Grade WSR 1105, PEO, Molecular Weight 900,000
Polymer Concentration Range: 2 to 15 wt. %
Propylene Glycol: 1 to 45%
Formula using WSR 1105
3.25% WSR 1105
18% USP propylene glycol
78.75% pyrogen free water

EXAMPLE 8

Grade WSR N-60K, PEO, Molecular Weight 2,000,000
Polymer Concentration Range: 0.1 to 6 wt. %
Formula using WSR N-60K
2% WSR N-60K
98% pyrogen free water

EXAMPLE 9

Grade WSR N-60K, PEO, Molecular Weight 2,000,000
Polymer Concentration Range: 0.1 to 6 wt. %
Propylene Glycol: 1 to 45%
Formula using WSR N-60K
1.5% WSR N-60K
18% USP propylene glycol
80.5% pyrogen free water

EXAMPLE 10

Grade WSR 301, PEO, Molecular Weight 4,000,000
Polymer Concentration Range: 0.1 to 6 wt. %
Formula using WSR 301
2% WSR 301
98% pyrogen free water

EXAMPLE 11

Grade WSR 308, PEO, Molecular Weight 8,000,000
Polymer Concentration Range: 0.05 to 6 wt. %
Formula using WSR 308
1% WSR 308
99% pyrogen free water Subsequent to evaluation of data gathered from evaluation of solutions prepared from the above-mentioned Sentry NF Grades, WSR-1105 (900,000 mw.) and WSR-205 (600,000 mw.) were selected as the as the preferred polymers of this embodiment of the inventive device.

The preferred formula for the embodiment of this inventive device of an in vivo biocompatible, biodegradable ultrasound couplant is the formula of Example 4 that utilizes Sentry NF WSR-205. The molecular weight (nominally 600,000) of this grade of polymer creates acceptable viscosities and rheologies at polymer concentrations of 5% and less, preferably 4.5%. Sentry NF WSR-205, was selected as the preferred polymer grade due to factors related to appearance, adhesion characteristics, rheology, ease of manufacture and economic factors. The most preferred formulation as the embodiment of this device is that of Example #5 which is constituted as a 4% solution of WSR-205 with water and 18 wt. % propylene glycol, and produces viscosities of +/−4,000 centipoise as measured with a Brookfield viscometer using a #2 LVT spindle at 1.5 rpm. Production of polymer solutions having such viscosity at a 4% polymer concentration, results in polymer costs savings and acceptable physical characteristics. Higher polymer concentrations increase product costs, decrease clarity and adversely affect tactile characteristics. Sentry grade WSR-301, molecular weight 4,000,000, and the highest available molecular weight (8,000,000) resin WSR-308, produces equivalent viscosities with less polymer and greater clarity than a 4% solution of WSR-205, however; they are less suitable for ultrasound use due to less desirable adhesive and tactile characteristics. Unlike transcutaneous gels of the prior art, a 4% solution of WSR-205 is pseudo-plastic and has sufficient tack to adhere to the active face of the transducer and internal surface of a probe cover to maintain desired acoustic coupling during rigorous ultrasound exams.

In procedures where an ultrasound probe is covered by a protective sheath as previously mentioned, the ultrasound couplants of the present invention not only provide acceptable lubricating and/or acoustic coupling properties on the outside of the protective sheath but also within the sheath (i.e. between the ultrasound probe and the sheath). Thus, in the event of rupture of the sheath, spillage of the inventive ultrasound couplant into a body cavity will not adversely affect the patient due to the in vivo biocompatibility of the couplants of the present invention.

In the same manner, puncture procedures under ultrasound imaging guidance, such as needle biopsies, can benefit from the present invention in that the ultrasound couplant carried by the needle into the body will be an in vivo biocompatible couplant thus posing no harm to body cavity tissue.

It is also within the scope of the present invention to apply the inventive couplant directly to an organ or tissue, such as the eye, and then proceed with ultrasound imaging by contacting the couplant-coated organ or tissue with the active area of a transducer.

It is to be understood that while the present invention has been discussed with reference to medical ultrasound applications within a human body, it is not to be limited thereto. The present invention is also contemplated to be applicable within other animals such as in veterinary ultrasound.

While the invention has been described with reference to preferred embodiments it is to be understood that the invention is not limited to the particulars thereof. The present invention is intended to include process, formulation and modifications which would be apparent to those skilled in the art to which the subject matter pertains without deviating from the spirit and scope of the appended claims.

What is claimed is:

1. A method of conducting ultrasound energy between an ultrasound transducer and a target to be imaged from within a body cavity, said method comprising:

providing said transducer with an active area for transmitting and receiving said ultrasound energy, applying an ultrasound couplant to at least one of said target, said transducer, within a transducer cover fitted onto said transducer, and on the exterior of a transducer cover fitted onto said transducer, said couplant being in vivo biocompatible and comprising polyethylene oxide in a concentration amount of about 0.05 wt. % to about 65 wt. %, the balance water, said couplant having acoustic properties generally equivalent to acoustic properties of said target, placing said transducer into said body cavity aided by the lubricity of said couplant with said active area in contact with said couplant on said target, transmitting and receiving said ultrasound energy respectively to and/or from said target through said ultrasound couplant, whereby subsequent to said transmitting and receiving, said transducer is removed from said cavity and said couplant remains within the body cavity by design or by accident, where it is biodegradable, bio-inert or bioerodable with respect to said target and said body cavity.

2. The method of claim 1 wherein said ultrasound couplant further comprises polyalkylene glycol in the amount of 1 to 45 wt. %.

3. The method of claim 2 wherein said polyalkylene glycol comprises propylene glycol.

4. A method of conducting ultrasound energy between an ultrasound transducer and a target, said method comprising:

providing said transducer with an active area for transmitting and receiving said ultrasound energy, arranging an ultrasound conducting sheath outwardly of said transducer active area, providing an ultrasound couplant between said active area and said sheath, said couplant being in vivo biocompatible and comprising polyethylene oxide in a concentration amount of about 0.05 wt. % to about 65 wt. %, and the balance water, said couplant having acoustic properties generally equivalent to acoustic properties of said target, placing said couplant on said target if said target is located externally on a body, placing the covered transducer on said target, transmitting and receiving said ultrasound energy respectively to and/or from said target through said sheath and said ultrasound couplant.

5. The method of claim 4 wherein said ultrasound couplant further comprises polyalkylene glycol in the amount of 1 to 45 wt. %.

6. The method of claim 5 wherein said polyalkylene glycol comprises propylene glycol.

7. In an ultrasound guided needle puncture procedure wherein an ultrasound transducer is utilized to guide said needle through skin of a patient and into a target within the body of said patient, the improvement comprising:

applying an ultrasound couplant on said skin, said couplant being in vivo biocompatible and comprising polyethylene oxide in a concentration amount of about 0.05 wt. % to about 65 wt., the balance water, carrying out said needle puncture procedure utilizing said ultrasound transducer to guide said needle to said target, whereby couplant carried by said needle into said body during the procedure remains in said body where it is biodegradable, bio-inert or bioerodable with respect to said body.

8. The procedure of claim 7 wherein said ultrasound couplant further comprises polyalkylene glycol in the amount of 1 to 45 wt. %.

9. The method of claim 8 wherein said polyalkylene glycol comprises propylene glycol.

* * * * *